(12) United States Patent
Quearry (10) Patent No.: US 9,872,666 B2
(45) Date of Patent: Jan. 23, 2018

(54) ECHOGENIC SURFACE USING REULEAUX TRIANGLE

(71) Applicant: Muffin Incorporated, West Lafayette, IN (US)

(72) Inventor: Benjaman B. Quearry, Bloomington, IN (US)

(73) Assignee: Muffin Incorporated, West Lafayette, IN (US)

( * ) Notice: Subject to any disclaimer, the term of this patent is extended or adjusted under 35 U.S.C. 154(b) by 547 days.

(21) Appl. No.: 14/199,115

(22) Filed: Mar. 6, 2014

(65) Prior Publication Data

US 2014/0276073 A1    Sep. 18, 2014

Related U.S. Application Data

(60) Provisional application No. 61/782,890, filed on Mar. 14, 2013, provisional application No. 61/783,043, filed on Mar. 14, 2013.

(51) Int. Cl.
*A61B 5/05*     (2006.01)
*A61B 8/00*     (2006.01)
(Continued)

(52) U.S. Cl.
CPC .......... *A61B 8/4455* (2013.01); *A61B 8/0841* (2013.01); *A61B 17/3421* (2013.01); *A61B 90/39* (2016.02); *A61B 8/4483* (2013.01); *A61B 8/58* (2013.01); *A61B 2017/00526* (2013.01); *A61B 2017/00725* (2013.01); *A61B 2017/3413* (2013.01); *A61B 2090/3925* (2016.02)

(58) Field of Classification Search
CPC ..... A61B 8/4455; A61B 90/39; A61B 8/0841; A61B 17/3421; A61B 2017/00526; A61B 2017/00725; A61B 2090/3925; A61B 2017/3413; A61B 8/4483; A61B 8/58
USPC ......................................... 600/437–469, 424
See application file for complete search history.

(56) References Cited

U.S. PATENT DOCUMENTS 4,055,167 A    10/1977  Bernstein
4,207,901 A *  6/1980  Nigam ..................... A61B 8/00
                                                     367/151
(Continued)

FOREIGN PATENT DOCUMENTS

DE            2425724       11/1975
DE     20 2009 005 135 U1    4/2010
(Continued)

OTHER PUBLICATIONS

English Abstract of JP 2012-525886A to B Braun Melsungen Ag, translation date not provided.
(Continued)

*Primary Examiner* — Sanjay Cattungal
(74) *Attorney, Agent, or Firm* — Woodard, Emhardt, Moriarty, McNett & Henry LLP (57) ABSTRACT

Disclosed are embodiments of devices and methods for providing enhanced echogenicity to medical devices. An echogenic feature is formed in the shape of a pyramidal reuleaux triangle. A lobe is constructed at a rim of an echogenic feature to create a pocket between the lobe and a bottom surface of the feature. A test fixture is disclosed which provides a method for obtaining quantifiable echogenicity data of medical devices.

19 Claims, 8 Drawing Sheets

(51) Int. Cl.
*A61B 8/08* (2006.01)
*A61B 17/34* (2006.01)
*A61B 90/00* (2016.01)
*A61B 17/00* (2006.01)

(56) References Cited

U.S. PATENT DOCUMENTS

| | | | |
|---|---|---|---|
| 4,401,124 A * | 8/1983 | Guess | A61B 8/0833 600/458 |
| 4,411,657 A | 10/1983 | Galindo | |
| 4,490,139 A | 12/1984 | Huizenga et al. | |
| 4,566,438 A | 1/1986 | Liese et al. | |
| 4,582,061 A | 4/1986 | Fry | |
| 4,627,444 A | 12/1986 | Brooker | |
| 4,702,260 A | 10/1987 | Wang | |
| 4,708,147 A | 11/1987 | Haaga | |
| 4,791,937 A | 12/1988 | Wang | |
| 4,799,495 A | 1/1989 | Hawkins et al. | |
| 4,869,259 A | 9/1989 | Elkins | |
| 4,900,300 A | 2/1990 | Lee | |
| 4,903,709 A | 2/1990 | Skinner | |
| 4,977,897 A | 12/1990 | Hurwitz | |
| 4,989,614 A | 2/1991 | Dejter, Jr. et al. | |
| 4,991,592 A | 2/1991 | Christ | |
| 5,048,530 A | 9/1991 | Hurwitz | |
| 5,106,364 A | 4/1992 | Hayafuji et al. | |
| 5,161,542 A | 11/1992 | Palestrant | |
| 5,221,269 A | 6/1993 | Miller et al. | |
| 5,320,110 A | 6/1994 | Wang | |
| 5,383,466 A | 1/1995 | Partika | |
| 5,425,376 A | 6/1995 | Banys et al. | |
| 5,449,001 A | 9/1995 | Terwilliger | |
| 5,458,112 A | 10/1995 | Weaver | |
| 5,470,308 A | 11/1995 | Edwards et al. | |
| 5,490,521 A | 2/1996 | Davis et al. | |
| 5,535,755 A | 7/1996 | Heske | |
| 5,553,477 A | 9/1996 | Eisensmith et al. | |
| 5,807,304 A | 9/1998 | Cockburn | |
| 5,817,033 A | 10/1998 | DeSantis et al. | |
| 5,829,439 A | 11/1998 | Yokosawa et al. | |
| 5,865,765 A | 2/1999 | Mohajer | |
| 5,934,212 A | 8/1999 | Gitlin et al. | |
| 5,967,988 A | 10/1999 | Briscoe et al. | |
| 5,971,939 A | 10/1999 | DeSantis et al. | |
| 6,053,870 A * | 4/2000 | Fulton, III | A61B 17/3421 600/458 |
| 6,663,592 B2 | 12/2003 | Rhad et al. | |
| 6,709,408 B2 | 3/2004 | Fisher | |
| 7,258,669 B2 | 8/2007 | Russell | |
| D657,461 S | 4/2012 | Schembre et al. | |
| 8,617,079 B2 * | 12/2013 | Mitchell | A61B 8/0833 600/437 |
| 2003/0158480 A1 | 8/2003 | Tornes et al. | |
| 2004/0249288 A1 * | 12/2004 | Ichikawa | A61B 8/0841 600/464 |
| 2008/0097213 A1 | 4/2008 | Carlson et al. | |
| 2009/0054773 A1 | 2/2009 | Shizuka | |
| 2009/0137906 A1 * | 5/2009 | Maruyama | A61B 5/1422 600/461 |
| 2010/0317996 A1 | 12/2010 | Dillon | |
| 2011/0046619 A1 | 2/2011 | Ducharme | |
| 2011/0160592 A1 | 6/2011 | Mitchell | |
| 2011/0313288 A1 | 12/2011 | Chi Sing et al. | |
| 2012/0059247 A1 | 3/2012 | Speeg et al. | |
| 2012/0059250 A1 | 3/2012 | Gray et al. | |
| 2012/0253228 A1 | 10/2012 | Schembre et al. | |
| 2012/0253297 A1 | 10/2012 | Matsuzawa | |
| 2013/0267942 A1 | 10/2013 | Fulton, III | |

FOREIGN PATENT DOCUMENTS

| | | |
|---|---|---|
| EP | 0 019 104 A2 | 4/1980 |
| EP | 0 127 781 A2 | 12/1984 |
| EP | 0 624 342 A1 | 11/1994 |
| EP | 1 426 011 A1 | 6/2004 |
| JP | H08 206118 A | 8/1996 |
| JP | 2006-271874 | 10/2006 |
| JP | 2011-067641 | 4/2011 |
| JP | 2012-513833 | 6/2012 |
| JP | 2012-525886 A | 10/2012 |
| KR | 10-2011-0048546 A | 5/2011 |
| WO | WO 2008/062451 A2 | 5/2008 |
| WO | WO 2010/078151 A1 | 7/2010 |
| WO | WO 2012/133276 A1 | 10/2012 |

OTHER PUBLICATIONS

English Abstract of KR 10-2011-0048546A to CoCo Res Pty Ltd., translation date not provided.
International Search Report and Written Opinion issued in PCT/US2014/021052, dated May 29, 2014.
DE 20 2009 005 1350U1 Machine Translation.
DE 2425724 English Abstract.
EP 0 019 104 A2 English Abstract.
JP 2006-271874 English Astract.
Sviggum et al., "Needle Echogenicity in Sonographically Guided Regional Anesthesia", American Institute of Ultrasound in Medicine, J Ultrasound Med 2013; 32:143-148.
WO 2012/33276 A1 English Abstract.
Machine Translation of JP 2011-067641, obtained Aug. 2, 2017.
English Abstract of JP H08-206118, obtained Mar. 3, 2017.

* cited by examiner

ECHOGENIC SURFACE USING REULEAUX TRIANGLE

REFERENCE TO RELATED APPLICATIONS

This application claims the benefit of U.S. Provisional Patent Application No. 61/782,890, filed Mar. 14, 2013, and U.S. Provisional Patent Application No. 61/783,043, filed Mar. 14, 2013, which are hereby incorporated by reference in their entireties.

FIELD

The present disclosure concerns devices and methods for ultrasound use within the human body, including devices and methods for enhancing ultrasound visibility.

BACKGROUND

Medical devices for subcutaneous use are known in the medical field. For example, biopsy needles are used to capture and remove internal tissues while avoiding invasive surgery. When performing medical procedures, often targeted bodily areas are surrounded by blood vessels or internal organs which can cause difficulties with accurate percutaneous positioning of medical devices. Imaging methods can mitigate some of these difficulties by providing for simultaneous imaging of internal organs and medical devices. Ultrasound imaging is particularly suitable due to its lesser operation cost and increased portability in comparison to other imaging modalities such as X-ray and MRI. During ultrasound imaging procedures, a transducer emits ultrasound waves. A portion of the ultrasound waves reflect when encountering organs, tissues, and other items inside the body and then return to the transducer. The returned sound waves are then used to produce a visual representation of an internal cavity. This provides a real-time moving image of the internal organs and medical device which a physician can use to guide the medical device to the desired bodily area.

Problems exist with current uses of ultrasound imaging to place a medical device subcutaneously because the image obtained through ultrasound is not always clear. Several factors can affect ultrasonic visibility of a medical device. For example, the density of the material that the device is constructed of, the surface structure of the device, and the angle of the device relative to the transducer each affect ultrasonic visibility of the device. When the image clarity suffers, the observation and positioning of the medical device can be more imprecise. This can enhance the risk of inadvertent damage to surrounding tissues or incorrect tissue excision in the case of biopsy.

To increase image clarity, echogenic enhancements which cause an altered or improved reflective response of ultrasound waves can be applied to a medical device and can cause greater ultrasound image clarity of the device. This in turn can increase accuracy when positioning the medical device. For example, it is known to apply echogenic enhancements near the tip of a needle so that the tip location is known with greater accuracy. However, if the needle angle changes relative to the transducer angle, the quality of the signal reflected back to the transducer degrades. Additionally, while ultrasound technology has advanced to allow use of a wider range of ultrasound frequencies, standard echogenic enhancements allow the device to be clearly shown under a limited range of transducer frequencies. Thus, there is a need for echogenically-enhanced medical devices which can provide an ultrasound image that is more consistent and having better quality across a range of insertion angles and frequencies. Such echogenically-enhanced medical devices can improve the physician's confidence in placing a medical device.

Although medical devices can include features providing enhanced echogenicity, problems exist with quantifying values of echogenicity in order to compare echogenic response between multiple devices. Current testing of echogenicity is typically subjective and inaccurate for comparison testing. Current methods of clinical tests of echogenic devices often cannot quantify the reflective qualities of an echogenic device. This is particularly troublesome when multiple variables are added such as when attempting to test at various angular arrangements and frequencies. Some methods include animal studies, for example by inserting an echogenic needle to be tested into the tissue of an animal while viewing the needle on an ultrasound machine. This method provides many difficulties with obtaining usable and accurate data between different medical devices due to the variability of the testing procedure. Other proposed methods include inspecting the echogenic device optically with microscopy. However, this method cannot get a true representation of how a device will appear on an ultrasound image. Thus, there is a need for a device that will provide a cost-effective way to objectively and accurately compare the echogenicity of different medical devices.

SUMMARY

Among other things, disclosed are devices and methods for enhancing echogenicity of medical devices. In one example, a device surface includes at least one echogenic feature formed as a depression in the device surface. The feature has three feature surfaces, each intersecting the other feature surfaces. Each feature surface is concave toward the center of the feature. The device surface can have a plurality of the features, and in particular embodiments at least one of the features is oriented about its central axis at an angle that is different from the angle of an adjacent feature. Additionally or alternatively, at least one of the features can have a major dimension that is different from the major dimension of an adjacent feature, and/or at least one of the features can have a depth that is different than the depth of an adjacent feature.

In another example, a device surface has a plurality of echogenic features. At least one of the echogenic features is a depression in the device surface and has a rim and a bottom surface. The bottom surface is within (e.g. bounded at the device surface by and/or radially inward of) the rim and faces outward of the depression. The device surface further comprises a lobe extending over the depression, wherein a portion of the lobe faces the bottom surface and defines a pocket between the bottom surface and the lobe. The lobe can extend over substantially half of the depression. The at least one feature can have three feature surfaces, wherein each feature surface intersects the other feature surfaces, and wherein each feature surface is concave toward the center of the feature. The at least one feature can have three feature surfaces, wherein each feature surface intersects the other feature surfaces, and wherein at least one feature surface has a dimension aligned with the device surface that is different from a dimension aligned with the device surface of another feature surface.

In particular embodiments, the device surface can include at least one feature that is oriented about its central axis at an angle that is different from the angle of an adjacent feature. Additionally or alternatively, the device surface can include at least one feature that has a major dimension that is different from the major dimension of an adjacent feature, and/or at least one feature that has a depth that is different from the depth of an adjacent feature.

In another example, a cannula has a body portion and a tip portion, wherein the diameter of the cannula is tapered in the tip portion relative to the general diameter of the body portion. At least one depression is formed into the surface of the tip portion, wherein the depression has a depression surface, and wherein the surface normal at all points along the depression surface has vector components that point in a direction that is perpendicular to the cannula axis and/or toward the furthest extent of the tip portion. The depression can have a rim defined by the intersection between the depression surface and the surface of the cannula, and in specific examples the rim is generally shaped as a teardrop, the depression has a depression axis extending symmetrically relative to the depression and intersecting the rim, and/or the depression axis follows a path within a plane extending through the axis of the cannula. The cannula can have a plurality of depressions arranged about the tip portion. A plurality of depressions in the surface can include at least one of the depressions having a major dimension that is different from the major dimension of an adjacent depression, and/or at least one of the depressions having a depth that is different from the depth of an adjacent depression.

In another example, a device for measuring the echogenicity of the medical device includes a fluid container, a transducer having a viewing window, wherein the transducer is fixed to a transducer support which is rotatable about a first axis, a device support which is rotatable about a second axis, and wherein the device support is configured to position a portion of a medical device within the fluid container and within the viewing window. The device can further comprise visual indicator is showing the angular positions of the transducer support and the device support. The device can include the first axis being perpendicular to the second axis.

In another example, a method for measuring the visibility of a device through ultrasound includes placing a portion of a medical device in a fluid, fixing the medical device in a first position, capturing a first ultrasound image of the medical device, converting the first ultrasound image to grayscale, setting a visibility threshold value, and summing the pixels in the first ultrasound image which are greater than the threshold value. The method can further include fixing a second medical device in the first position, capturing a second ultrasound image of the second medical device, converting the second ultrasound image to grayscale, and summing the pixels in the second ultrasound image which are greater than the threshold value.

Further forms, objects, features, aspects, benefits, advantages, and embodiments of the present disclosure will become apparent from a detailed description and drawings provided herewith.

DESCRIPTION OF THE SELECTED EMBODIMENTS

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates. Embodiments are shown in detail, although it will be apparent to those skilled in the relevant art that some features that are not relevant to the present disclosure may not be shown for the sake of clarity.

Disclosed herein are embodiments of a medical device 20 suitable for endoluminal medical procedures. Device 20 has echogenic enhancements which make device 20 particularly suitable for use in conjunction with an ultrasound system. The echogenic enhancements include surface features which enhance, scatter, and/or redirect ultrasound signals. In some embodiments, the sizes of the features are varied to provide enhanced ultrasound signals at various ultrasound frequencies. The features are shaped and arranged to provide enhanced ultrasound signals at various spatial configurations (i.e. angles) between device 20 and an ultrasound transducer. In some cases, device 20 is used with a system that includes an ultrasound console (not shown) to provide subcutaneous imaging of device 20. The console portion can be connected to commercially available ultrasound probes with compatible pinout, or other medical devices which are configured for ultrasound imaging. The console is configured to process data obtained from an ultrasound transducer and in some cases creates image(s) viewable on a display or other data output.

As used herein, the term "echogenic" describes the characteristic ability of a surface or device to direct a relatively favorable quality and quantity of an ultrasound signal back to a transducer for imaging purposes in comparison to a surface or device (or portion thereof) which is less echogenic, non-echogenic, or echolucent. In other words, a device or surface with increased echogenicity (or greater echogenic response) provides enhanced ultrasound imaging capabilities compared to a device or surface which is less echogenic or more echolucent. As used herein, "echogenic" and "echogenicity" typically refers to characteristics of device 20 when device 20 is positioned within a body conduit or other such environment where fluids and/or body tissues surround device 20.

Figure 1:
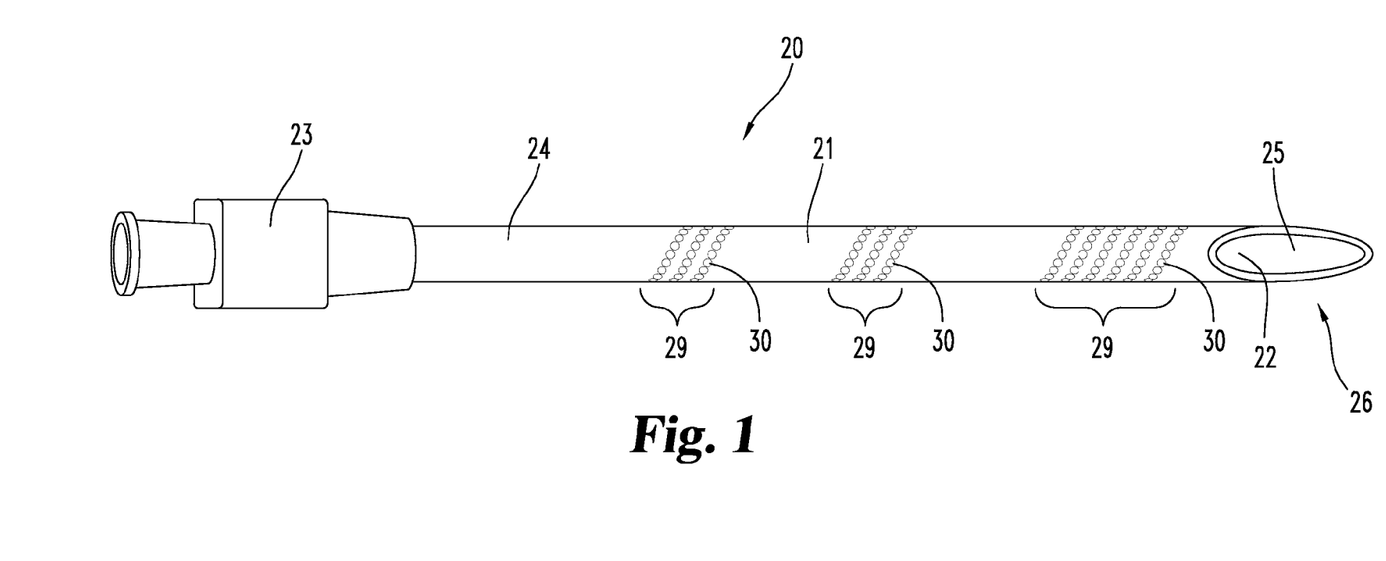
FIG. 1 is a top view of a medical device having echogenic regions.
Figure 2:
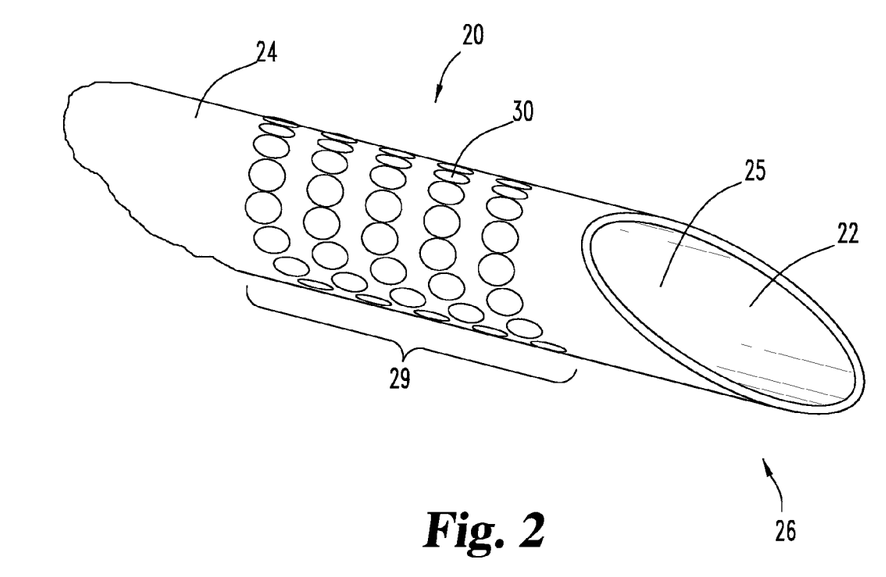
FIG. 2 is a partial perspective view of the tip of the medical device of FIG. 1.

Referring generally to FIGS. 1 and 2, embodiments of medical device 20 are illustrated. FIG. 1 shows an exemplary embodiment of device 20 which is in the form of a needle. It should be understood that device 20 could be any of a variety of types of medical devices which are used for percutaneous, subcutaneous or other internal applications involving ultrasound imaging and therapeutic techniques (e.g. biopsy needles, intravascular devices, laparoscopic tools, etc.). Device 20 in this embodiment includes a body 21, a tip 26, and a handle 23. Particular embodiments of device 10 are cylindrical, and are sized for insertion into a body without the need for an existing body conduit such as a blood vessel.

Body 21 in the illustrated embodiments is an elongated member, e.g. a tube or cannula having an outer surface 24 (i.e. device surface) and an inner surface 22 defining a lumen 25 (FIG. 2). Body 21 terminates at tip 26. Body 21 can be constructed of any suitable metal or polymer which is biocompatible and otherwise structurally appropriate for use as described herein.

Device 20 includes a control end which during use is nearest to the user and an application end which during use is nearest to the user's point of interest. The terms "control" and "application" are used throughout this description to describe these positional orientations. The control end of device 20 may extend outside of the patient during use. Alternatively, the control end may attach to another piece that extends outside the patient. The control end generally ends in a handle 23 or other operating portion for maneuvering device 20. Handle 23 can be any of a variety of forms or structures suitable for use in conjunction with needles or medical devices used in percutaneous applications. Handle 23 is generally constructed to be manipulatable by hand in some embodiments and has a hollow axis in communication with lumen 25 which can receive a stylet or other cylindrical objects.

The application end of the body 21 is formed as a beveled tip 26 in some embodiments. The bevel is generally constructed by cutting the cannula along a plane oblique to the lumen axis, i.e. a plane having a normal that is nonparallel to the lumen axis. Other embodiments of a body 21 may have alternative configurations. Tip 26 has cutting edges where the angle between the bevel surface and the outer surface is acute. Typically such bevels are capable of piercing or slicing tissue. Although the embodiment of tip 26 described herein is generally a planar cut configuration, other configurations of needle tips with varied cutting edges could be used.

Device 20 has one or more echogenic regions (e.g. echogenic regions 29) which are populated with a matrix (or population) of features 30 that enhance the echogenicity of device 20. The echogenic region is at least a portion of device 20, and in particular embodiments is at least a portion of surface 24.

Figure 3:
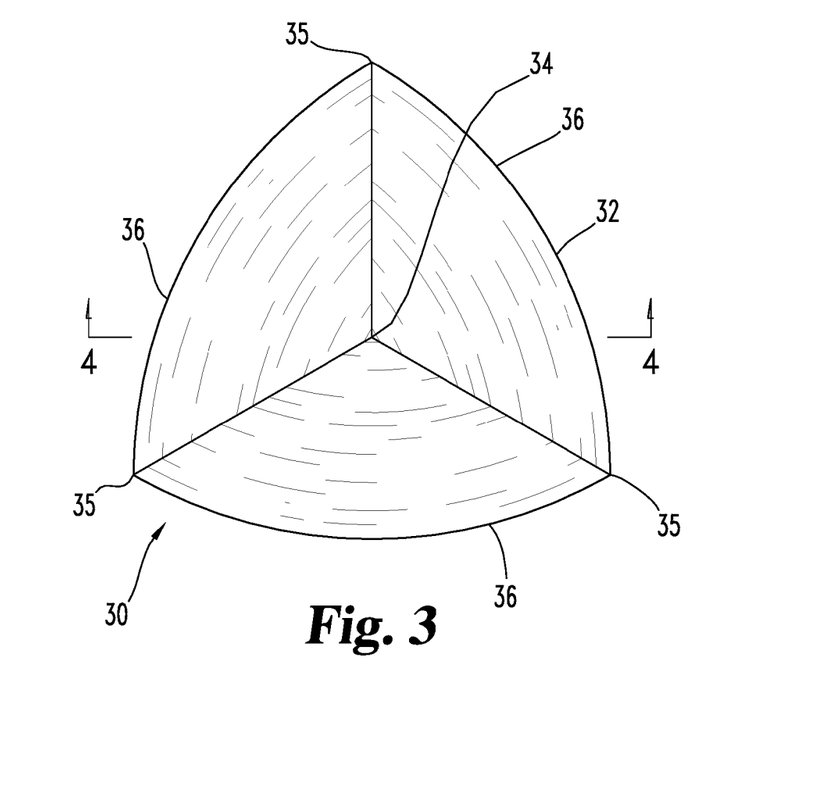
FIG. 3 is a top view of an echogenic feature in the form of a pyramidal reuleaux triangle.

Features 30 in some embodiments are generally a series of depressions in surface 24, which can have any of several possible geometric configurations. In the embodiment shown in FIGS. 3 and 4, feature 30 has three curved surfaces (i.e. feature surfaces), with each surface intersecting the other two surfaces. The surfaces extend between an apex 34 and a rim 32. Rim 32 generally represents the intersection of the surfaces of features 30 with surface 24. All three surfaces intersect or converge at apex 34. In that way, each feature 30 is constructed in a somewhat inverse pyramidal shape having curved surfaces and a central axis extending through apex 34. Each feature 30 has a profile at its rim 32 in the shape of a reuleaux triangle (see FIG. 3). Rim 32 has three points 35 which are equidistant to one another and three arcs 36 extending between the three points. The three arcs 36 are circular arcs with each having a radius equal to the distance between any two points 35. The reuleaux triangle profile is maintained throughout feature 30, such that a cross section taken generally parallel to rim 32 (or normal to the central axis) at any location between rim 32 and apex 34 has a similar reuleaux triangle profile. In that way, the three surfaces of feature 30 are turned inward or concave toward a center axis. In other words, in this embodiment, feature 30 takes the shape of the union of three cones, with each cone having an axis that intersects one of the points 35 as well as both axes of the other two cones.

Figure 5:
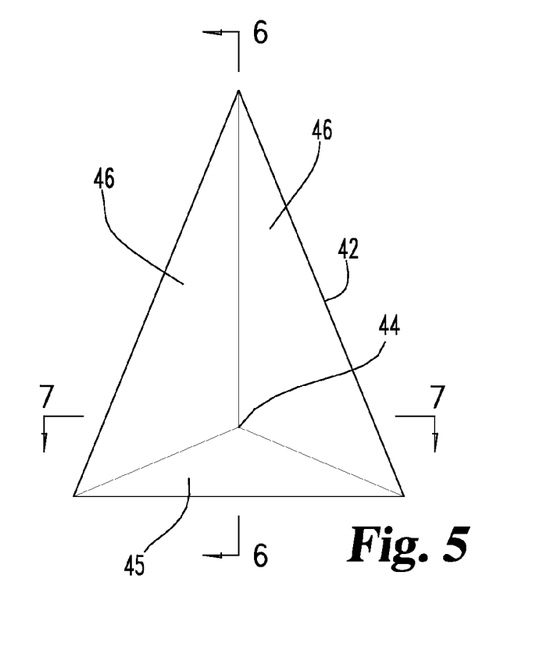
FIG. 5 is a top view of an echogenic feature in the form of a pyramidal isosceles triangle.

In other embodiments, feature 30 can be formed in other shapes. As another example (shown in FIGS. 5-7), feature 30 can be formed in the shape of a three-sided pyramid, with a triangle-shaped rim 42 and an apex 44. In the illustrated embodiment, rim 42 is shaped as an isosceles triangle. However, other shapes are suitable, such as equilateral, scalene, acute, right, and obtuse for example. In the illustrated embodiment, feature 30 has multiple surface angles. Surface 45 has an angle which is relatively close to perpendicular to surface 24 compared to the angle of surfaces 46 in relation to surface 24. In the illustrated embodiment, surface 45 is positioned on the application side of device 20 relative to surfaces 46.

Other embodiments of feature 30 can include a hemispherical shape, which when viewed at a cross section resembles a truncated half-hemisphere with a flat bottomed or round bottomed surface (not shown). Features 30 can be any of a variety of geometric configurations such as, for example, small cavities that are machined into surface 24, dimples, divots, grooves, lines, or ridges. Features 30 can be individually located in the cannula wall such that they are not in communication with each other or do not touch each other and are simply a series of individual geometric configurations. Alternatively, features 30 could be positioned in outer surface 24 as a continuous texture making the echogenic region substantially occupied by features 30.

In various embodiments, features 30 can be organized and positioned in a variety of configurations. The echogenic region(s) can be positioned at any point between the application side end of device 20 and the control side end of device 20. The echogenic region can occupy a portion or all of tip 26, a region adjacent to tip 26, or other parts of device 20. In the embodiment of FIGS. 1 and 2, an echogenic region is positioned near tip 26 so that not only can device 20 be located during ultrasound procedures but also tip 26 can be more accurately positioned during ultrasound procedures. In some embodiments, one or more echogenic regions are also positioned further from tip 26, and can be spaced a known distance apart to provide information to a user during ultrasound procedures, such as the distance of insertion of a needle or the proximity of the tip to certain body tissues (e.g. FIG. 1).

The embodiments of FIGS. 1 and 2 show features 30 arranged as a helical assortment within the echogenic regions, with each feature 30 being placed along a line representing a helical band about surface 24. In other embodiments, features 30 can be arranged in circumferential or longitudinal assortments about surface 24. Features 30 can be arranged in populations with varied densities across surface 24. Greater densities provide stronger echogenic response in some cases, such as, for example a helical configuration with tighter coils. Lesser densities provide lesser echogenic response in some cases, such as, for example, a helical configuration with looser coils. Generally, the density of arrangements of features 30 is chosen to provide a specific echogenic response. In some embodiments, features 30 are arranged in random patterns.

Figure 8:
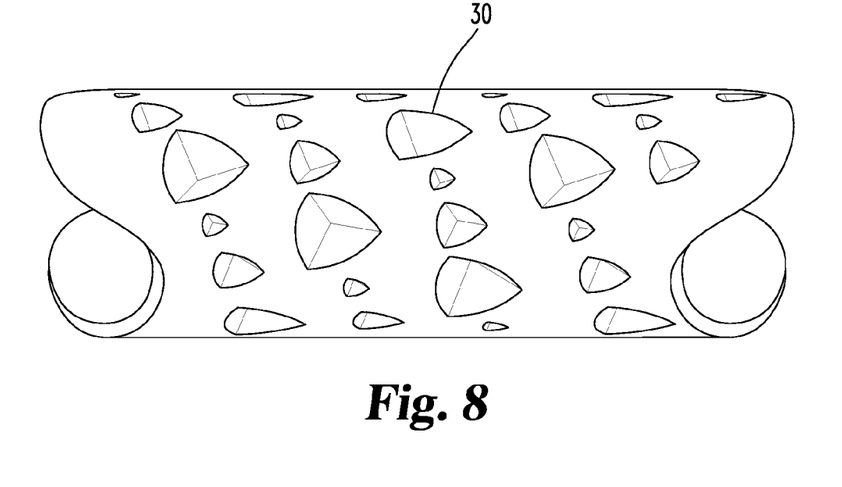
FIG. 8 is a partial perspective view of an embodiment of a medical device having echogenic features with varied major dimensions.

In some embodiments, characteristics of features 30 are varied. Variations can include differences among characteristics of features 30 relative to other features 30 within a population. Variations as described herein provide enhanced echogenic response across a range of ultrasound frequencies as well as consistent echogenic response across a range of relative angular orientations between the transducer and device 20. Variations can include, among others, differences in dimensions and shape as well as differences in angular orientation about the axes of individual features 30. Examples are shown in FIGS. 8 and 9 and are discussed in more detail below.

Figure 4:
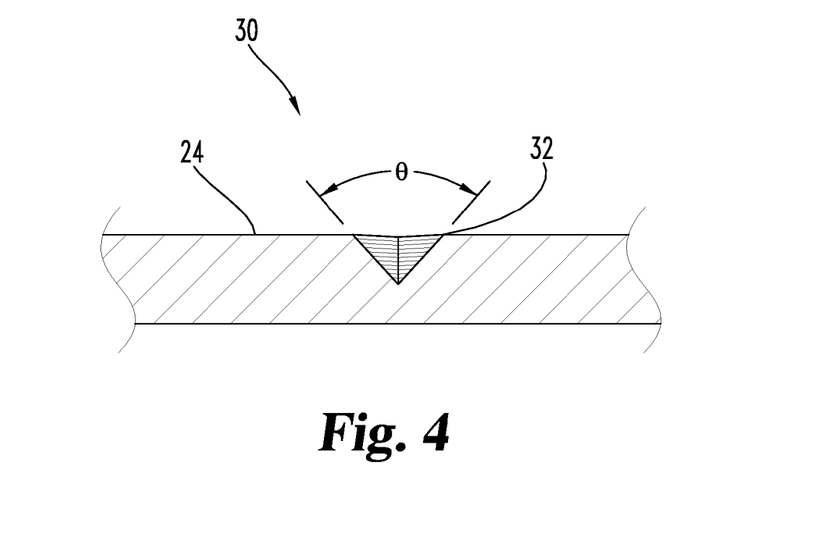
FIG. 4 is a side cross section of the echogenic feature of FIG. 3 taken along the line 4-4.
Figure 6:
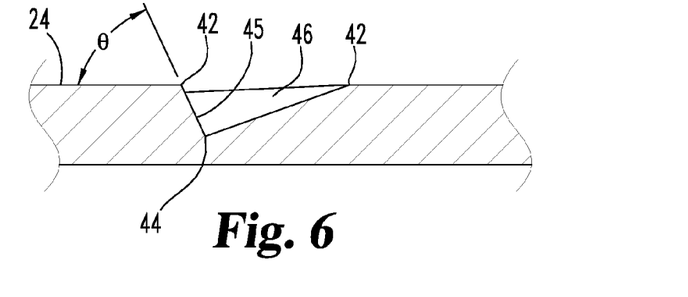
FIG. 6 is a side cross section of the echogenic feature of FIG. 5 taken along the line 6-6.
Figure 7:
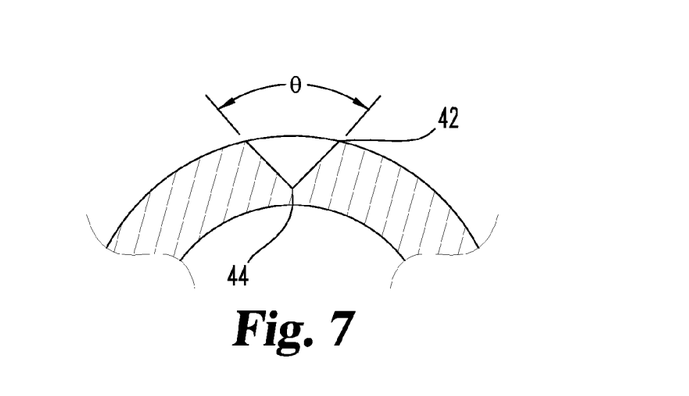
FIG. 7 is a side cross section of the echogenic feature of FIG. 5 taken along the line 7-7.

Several dimensions of features 30 can be varied, such as the size of the rim, the depth of the depression (i.e. the radial distance between apex 34 surface 24), and the angle of the walls (i.e. surfaces of features 30) relative to each other (see θ, FIGS. 4, 6, and 7). Each feature 30 has a major dimension which is generally a diameter of a circular area occupied by the rim or vertices of each feature 30. In the illustrated embodiment (FIG. 8), features 30 are formed with three different rim sizes, with each rim size having a different major dimension. In some embodiments, features 30 are formed with three different rim sizes, with each rim size having a different major dimension (e.g. with radii of 0.001 inches, 0.002 inches, and 0.003 inches). The rim sizes alternate in sequence within the helical bands, with the largest size being positioned between a small size and a medium size, and the medium size being positioned between a large size and a small size. In other embodiments, more or less rim sizes can be used, and the varied sizes can be arranged in other sequences or randomly.

In other embodiments, the depth of features 30 varies over a set range. This variance can extend even to features 30 having the same rim size. Similarly, the relative angles between the walls (or surfaces) of features 30 can vary. In embodiments having features 30 shaped as a reuleaux triangle, two of the three dimensions (rim size, depth, and angle θ) can be varied with the third variable being defined by the other two variables. In embodiments having features 30 with rims shaped as triangles, many of the dimensions can be varied such as the rim size, depth, both angles θ, the shape of the rim triangle, and the location of apex 44 relative to the rim of the triangle. In embodiments having features 30 with hemispherical shapes, the depth and diameter of the rim can both be varied. Particular embodiments include any number of differently dimensioned echogenic features 30. For example, device 20 could include as many as 10, 20, or 50 uniquely dimensioned features 30.

Figure 9:
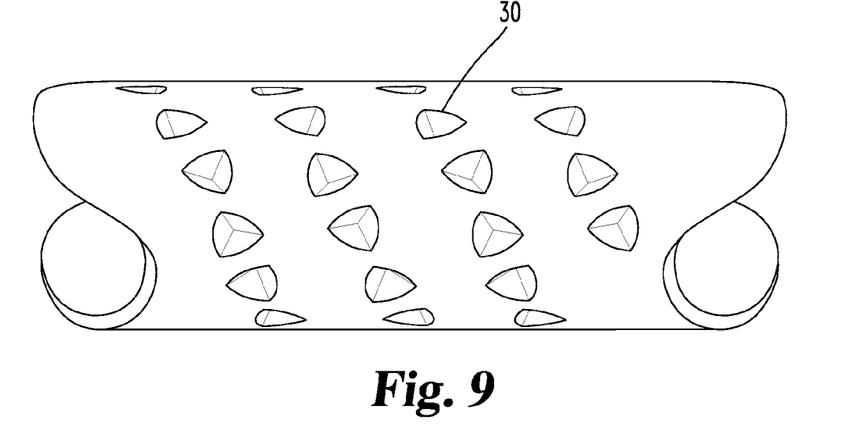
FIG. 9 is a partial perspective view of an embodiment of a medical device having echogenic features with varied angular orientations
Figure 10:
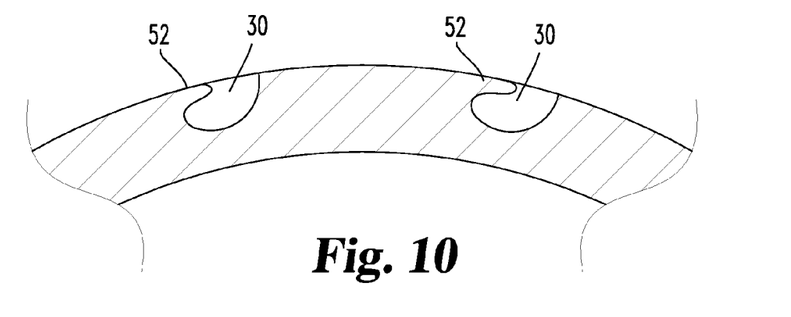
FIG. 10 is a cross section view of a portion of a medical device having echogenic features and a lobe.
Figure 11:
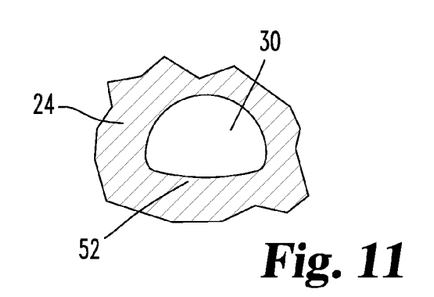
FIG. 11 is a top view of an echogenic feature having a lobe.
Figure 12:
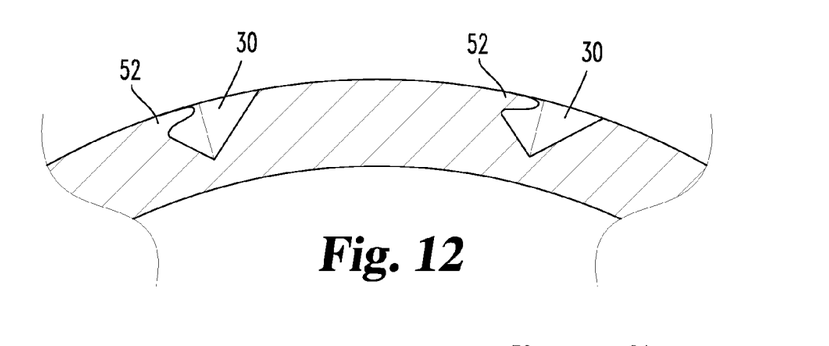
FIG. 12 is a cross section view of a portion of a medical device having echogenic features and a lobe.
Figure 13:
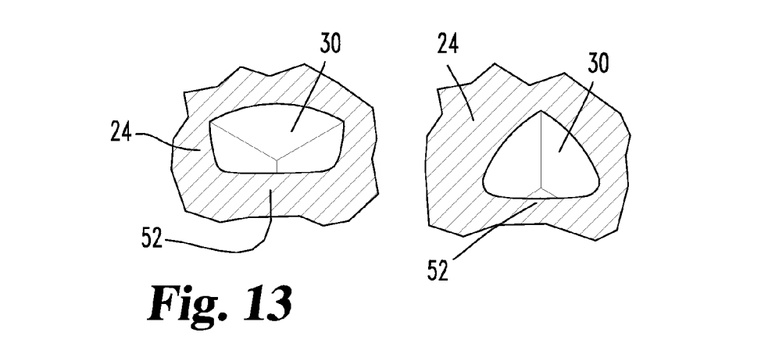
FIG. 13 is a top view of echogenic features having lobes.

In particular embodiments, features 30 are arranged with different angular orientations relative to one another, as shown in the embodiment of FIG. 9. In other words, features 30 can be arranged with a sequential angular rotation. For example, in the embodiment of FIG. 9, features 30 are alternatingly rotated 180° along the helical band. In other embodiments, sequential angular rotations can have a different value (e.g. 30°). In some embodiments, the sequential angular rotation values can be randomly chosen and dispersed throughout the population of features 30. In some embodiments, features 30 are configured and arranged with a combination of variance in both dimensions and angular orientations.

In certain embodiments, differently shaped features 30 are combined to co-populate device 20 and/or the echogenic regions. As examples, features 30 having a reuleaux triangle profile can be interspersed with features 30 having a hemispherical shape or features 30 having a triangular profile can be interspersed with features having a reuleaux triangle profile. In other embodiments, different profiles of features 30 with each having different dimensions and or angular orientations relative to one another are placed within particular populations of features 30.

Features 30 can be further varied by including a lobe 52 which extends over a portion of the depression (see FIGS. 10-13). Lobe 52 is generally a feature coupled with an echogenic feature 30 as already described. Lobe 52 is formed from the material of device 20 (or from the same material attached to device 20) in this embodiment and generally extends from or between one or more edges of the rim and over a portion of the depression. Lobe 52 generally extends over less than half of the depression, although in some embodiments lobe 52 extends over more than half of the depression. In other words, lobe 52 generally extends from about less than half the length of the rim. Lobe 52 defines a pocket between it and a bottom surface of the depression. The bottom surface of the depression is generally a portion of the surfaces of features 30 surrounding the apex. The bottom surface faces outward of the depression through the area defined by the rim, or that area which would be defined by the rim in absence of the lobe.

The pocket created by lobe 52 can be used to trap air, $CO_2$, contrast agent, bodily fluid or other material. Upon insertion of device 20, the bubble created in the pocket causes scattering of ultrasound signals so that at least a portion of an ultrasound signal is directed back to towards the transducer. This works in conjunction with the reflective capability of surfaces features 30 to greatly improve the echogenicity of device 20.

Lobe 52 can be created through certain manufacturing processes. For example, in some cases features 30 are created through use of a punch or roller to strike or impact surface 24, which creates the depression. In such cases, the impact force can be tailored to create a ridge around the rim. The ridge is a raised portion of the rim which extends radially further than the radially outermost extent of surface 24. Device 20 can then be rolled against the surface of a roller or other tool having a smooth and hard surface. Device 20 is rolled against the roller surface with sufficient force to push a portion of the ridge into the depression, thereby creating lobe 52. The remaining portion of the ridge is pushed into surface 24, leaving no material extending radially further than the radially outermost extent of surface 24.

Such a manufacturing method serves at least two purposes. First, it causes increased echogenicity as is explained below. Second, it allows surface 24 having features 30 to have a smoothness which is the same or close to the smoothness of a similar surface having no features 30. In other words, the value of the static and kinetic friction coefficients (in the context of bodily applications) of surface 24 are relatively unchanged or minimally changed during the manufacturing process. Such manufacturing techniques are described in U.S. Provisional Patent Application Ser. No. 61/783,043, entitled "Echogenic Surfaces with Pressed-Dimple Formations," filed on Mar. 14, 2013, and incorporated herein by reference.

During use, device 20 is inserted into a body conduit either through puncture or through an existing body conduit. An ultrasound imaging system including a console is used to image device 20 during insertion and while maneuvering device 20 to a desired location within the body. The ultrasound imaging system includes a transducer which is applied to the external surface of the body. The transducer transmits ultrasound signals generally towards device 20. Device 20 scatters and/or reflects a certain amount of the ultrasound signal back to the transducer. The transducer receives the returned ultrasound signal and transmits appropriate information to the console. The console displays an image which shows device 20 surrounded by body tissues and fluids. It is preferable for device 20 to appear with greater clarity and brightness than the surrounding body tissues and fluids. This is achieved by providing device 20 with enhanced echogenic properties. Features 30 provide device 20 with enhanced echogenic properties. Use of such echogenic features enhances echogenicity as compared to a smooth surface for a similar object. Device 20 having features 30 with varied dimensions and angular orientations is capable of providing enhanced ultrasound visualization throughout a wide range of ultrasound frequencies and relative angles between device 20 and the transducer.

Figure 14:
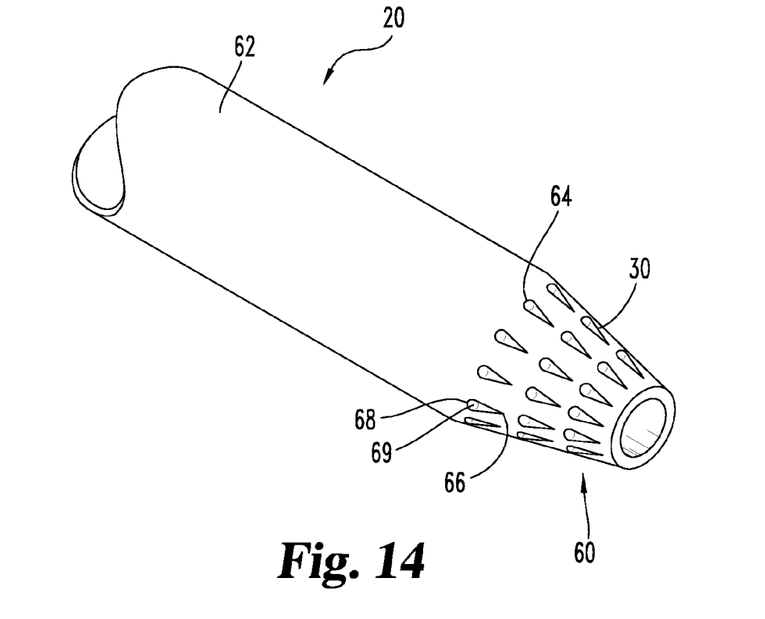
FIG. 14 is a partial perspective view of an end of a medical device having echogenic features in the shape of sectioned teardrops.
Figure 15:
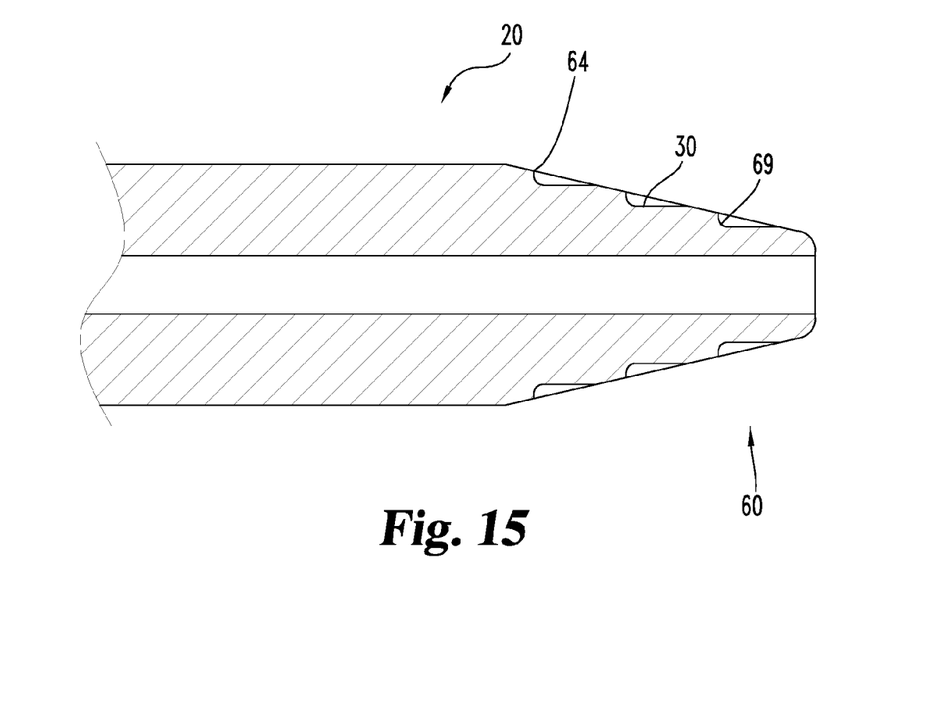
FIG. 15 is a cross section view of the tip of the medical device of FIG. 14 having echogenic features.

An alternative embodiment of a device 20 is shown in FIGS. 14 and 15. In that embodiment, device 20 is a catheter or other elongated medical device formed generally as a cannula as previously described. Device 20 has a body portion 62 and a portion which is a tip 60. Tip 60 tapers from body portion 62 towards the furthest application side end of tip 60. In other words, tip 60 has a gradually reduced external diameter between body portion 62 and the furthest application side end of tip 60.

Device 20 includes at least one or a series of features 30 positioned on the surface of tip 60. Features 30 are depressions formed in surface 24. Features 30 have a rim 64 which is shaped generally in a teardrop shape in surface 24, having an acute end 66 and a blunt end 68. Acute end 66 is positioned on the application side end of rim 64, and rounded end 68 is positioned on the control side end of rim 64. Features 30 have a surface 69 (i.e. a depression surface) which is bounded on all sides by rim 64. In other words, rim 64 is defined by an intersection between surface 69 and surface 24. The depressions have an axis extending symmetrically through the depressions which follows a path within a plane extending through the center axis of device 20. Features 30 are constructed so that the surface normal at all points along surface 69 has vector components that point either perpendicular to the center axis of device 20 and/or toward the furthest extent of the application side of tip 60. In other words, at no point along surface 69 does the surface normal have a vector component pointing toward the control end of device 20.

Device 20 in the FIGS. 14 and 15 embodiment can be constructed by injection molding. A mold can include features 30. The teardrop shape of rim 64 and tapered shape of tip 60 allows device 20 and each feature 30 to be withdrawn from the mold towards the control side of device 20 without damaging features 30 or altering the shape of features 30. This unique shape and method of manufacture provides a way to efficiently and quickly manufacture features 30 into a medical device.

Figure 16:
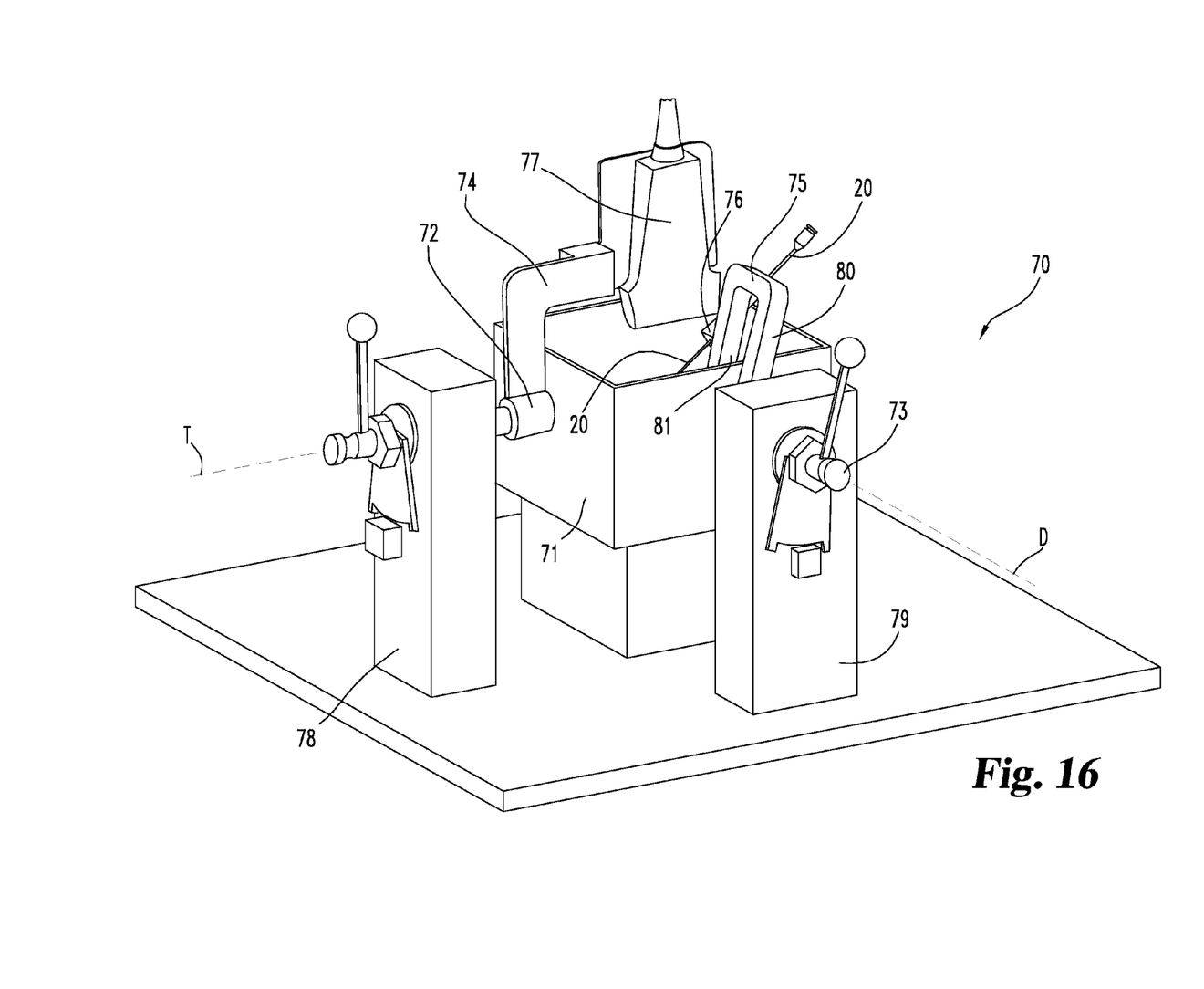
FIG. 16 is a perspective illustrative view of a test fixture for testing echogenicity of medical devices.

A further concept of the present disclosure includes an echogenicity test fixture 70 as shown in FIG. 16. Test fixture 70 includes fluid container 71, spindles 72 and 73, clamp plate 74, yoke 75, device mount 76, transducer 77, and supports 78, 79. Fluid container 71 is a container having a base and a plurality of walls and is capable of holding a fluid. Spindle 72 is mounted rotatably and horizontally to support 78. Spindle 72 has a handle and a locking system which allows spindle 72 to be fixed at particular angular positions about a transducer axis T. Similarly, spindle 73 is mounted rotatably and horizontally to support 79. Spindle 73 has a handle and a locking system which allows spindle 73 to be fixed at particular angular positions about a device axis D. The locking systems provide a way for spindles 72, 73 to be positioned in a variety of precisely repeatable angular positions while also providing a visual indication of the angular positions. In some embodiments, spindle 73 is mounted perpendicular relative to spindle 72. Similarly, transducer axis T is perpendicular to a device axis D in some embodiments. In such case, fluid container 71 is positioned at the intersection of transducer axis T and device axis D, and in some embodiments fluid container 71 is placed upon a support.

Transducer 77 is fixedly attached to clamp plate 74 (i.e. support) by any of a variety of known suitable attachment methods. Clamp plate 74 is fixed to spindle 72 so that it rotates about transducer axis T in response to rotation of spindle 72. Similarly, transducer 77 rotates about transducer axis T in response to rotation of spindle 72. Yoke 75 (i.e. support) is fixed to spindle 73 so that it rotates about device axis D in response to rotation of spindle 73. Similarly, device mount 76 rotates about device axis D in response to rotation of spindle 73. Yoke 75 has furcations which straddle a wall of fluid container 71, with one furcation 80 positioned external to fluid container 71 and the other furcation 81 positioned partially within fluid container 71.

Device mount 76 is fixed to furcation 81 by any of a variety of known and suitable attachment methods. Device mount 76 is structured to hold device 20 or any of a variety of elongated medical devices. When positioned within device mount 76, at least a portion of device 20 (usually the application end) is positioned below the rim of fluid container 71 (i.e. within fluid container 71). When fluid container 71 contains a fluid, a portion of device 20 is submerged within the fluid. Device mount 76 has a locking feature which fixes the position of device 20 so that device 20 is incapable of moving relative to yoke 75 during testing procedures.

Test fixture 70 provides a way to hold a medical device in a position within the viewing window of an ultrasound transducer while allowing the medical device and transducer to move through a range of positions.

Certain embodiments of device 20 as described herein were tested using test fixture 70. A typical testing procedure will be described. Prior to testing, fluid container 71 is filled partially with a fluid such as an oil or other substance having acoustic impedance similar to that of body fluids and tissues in order to simulate a bodily environment. Device 20 is mounted to device mount 76 such that the application end of device 20 (including echogenic features 30) is submerged within the fluid. Transducer 77 is activated and an ultrasound image is produced. The ultrasound image is captured digitally, saved, and retained for reference in future use. Device 20 and transducer 77 are moved sequentially through a range of positions during testing. For example, device 20 is positioned at angles of 30°, 35°, 40°, and 45° relative to a horizontal axis while transducer 77 is positioned with a viewing window aligned at angles of −15°, 0° (perpendicular to device 20), and 15° relative to device 20. The cumulative combination of these angles results in 12 positions. The 12 positions are each tested multiple times with transducer 77 emitting ultrasound signals at frequencies of 5 MHz, 7.5 MHz, and 10 MHz, for a combination of 36 configurations.

Images are captured of each of the 36 configuration for a variety of embodiments of device 20 as well as several embodiments of existing needles for medical use. A crop area of each image is captured. The crop area is constant and uniform for all of the images. The images are then converted to grayscale so that each pixel has a brightness value between 1 and 256. A certain value between 1 and 256 is chosen as a visibility threshold. For each image, a summation is taken of the number of pixels that are greater than the visibility threshold value. The summation value establishes a brightness rating for each configuration. The data is then stored and analyzed, in some cases by calculating a mean brightness rating with standard deviation.

Test fixture 70 provides quantifiable echogenicity data about medical devices by holding the needle and transducer at known and repeatable angles to gather image data for the measurement of echogenicity. Use of test fixture 70 removes any subjectivity in the testing process and provides a repeatable metric and quantifiable data. Accordingly, test fixture 70 provides valuable data which can be used to positively identify the most advantageous arrangements and configurations of echogenic features.

The test data obtained through use of test fixture 70 illustrates the advantages of the embodiments of device 20 as described herein, particularly when data is compared between device 20 and currently-used medical needles. For example, a device 20 having echogenic features 30 in the form of reuleaux triangles arranged with a variation in angular orientation was tested and compared to an existing needle having hemispherical dimples created from a punch method. That embodiment produced a mean brightness rating of 72502 with a standard deviation of 34176, which is a particularly good result compared to the existing needle which had a mean brightness rating of 33925 with a standard deviation of 23465. An even better result was achieved with an embodiment of device 20 produced through the rolling method and having lobes 52. That embodiment of device 20 had features 30 in the form of reuleaux triangles with lobes 52 and arrangement with variations in angular orientation. That embodiment produced a mean brightness rating of 87440 with a standard deviation of 48648, which is significantly improved relative to the existing needle.

Generally, an ultrasound signal is partially reflected at the interface of two mediums having differing acoustic impedances, such as a fluid and the surface of device 20. The reflected ultrasound signal is enhanced by providing device 20 with features 30 that are more effective at reflecting the ultrasound signal at its particular frequency. Testing results show that the reflective capabilities of such echogenic features are dependent on the dimensions of the features as well as the wavelength of the ultrasound signal. For example, when the major dimensions of features 30 are small compared to the wavelength of the signal, the ultrasound signal becomes diffuse upon interacting with the feature 30 and only a small portion of the signal is reflected back to the transducer. This is similar to fluid waves encountering a wall or feature which is small in comparison to the wavelength. In such circumstances, generally the waves collide and conflict with one another, resulting in overall dampening of the wave.

By incorporating features 30 which have varied dimensions, device 20 can be more effectively imaged using a variety of frequencies of ultrasound, as well as by multiple-frequency ultrasound transducers. For example, device 20 having features 30 with different dimensions and/or characteristics can effectively reflect (for imaging purposes) ultrasound signals having frequencies in the range of 1-20 MHz. Higher frequency ultrasound signals correspond with smaller dimensions, and lower frequency ultrasound signals correspond with larger dimensions. As an example, features 30 having a major dimension of 0.003 inches correspond with and most effectively reflect ultrasound signals having a frequency of 5 MHz. Because a specific ultrasound frequency reflects best from specifically dimensioned features 30, multiple sizes of features 30 allow device 20 to be imaged equally well at a variety of frequencies. In this way, a single device 20 can produce an enhanced ultrasound signal in conjunction with ultrasound transducers and ultrasound imaging equipment for a range of ultrasound frequencies.

Additional testing was performed in an attempt to determine the effects of various echogenic enhancements on the level of discomfort produced by a needle from insertion within a body. Testing was performed by measuring the insertion force of certain embodiments of device 20 and comparing to the measurements for various existing needles. The insertion force generally correlates with the level of discomfort. Although insertion force varies according to the distance of insertion, comparisons were made between the insertion forces at standardized depths among all of the tested medical devices. It was determined that embodiments of device 20 having features 30 in the shape of a reuleaux triangle, manufactured with the roller method described in U.S. Provisional Patent Application No. 61/783,043, and including lobes 52 require significantly less insertion force compared to other types of echogenically-enhanced needles. For example, such a device 20 has a load value of 0.270 N compared to 0.906 N required by a similar device 20 that does not include lobes 52. As mentioned previously, the surfaces 24 of devices 20 having lobes 52 and no ridge exhibit lower static and kinetic friction coefficients compared to devices 20 that have a ridge and do not have lobes 52.

In practice, due to manufacturing realities the actual shape of features 30 vary somewhat from the theoretical shapes described herein. In some cases, the tools used to create the depressions change shape slightly between the beginning and the end of their service life, which causes some variance in the actual shape of the depressions. In other cases, the materials of device 20 may have granular peculiarities or other characteristics which cause some of the features 30 to have a slightly different shape than the theoretical perfect shape. For example, features 30 created in the reuleaux triangle configuration described previously may not all have a single distinct point representing apex 34. However, it should be understood that features 30 operate as described herein even with slight variances in manufacturing.

While some of the above discussion concerned specific use in the context of ultrasound system applications, it will be understood that embodiments of device 20 could also be used for a variety of other medical procedures and with a variety of other medical devices.

Although particular materials were highlighted herein for some components of device 20, those materials are not intended to be limiting of the types of materials which are suitable to be used in device 20. Additionally, where materials were not highlighted, a variety of materials could be used such as certain types of metals, polymers, ceramics or other types of materials which are suitable for use in devices for small body cavity applications.

While the disclosure has been illustrated and described in detail in the drawings and foregoing description, the same is to be considered as illustrative and not restrictive in character, it being understood that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

What is claimed is:

1. A medical device comprising:
a device surface having at least one echogenic feature formed as a depression in the device surface, wherein the feature has three feature surfaces, wherein each feature surface intersects the other feature surfaces, and wherein each feature surface is curved and individually concave toward the center of the feature.

2. The device of claim 1, the device surface further comprising a plurality of the features, wherein at least one of the features is oriented about its central axis at an angle that is different from the angle of an adjacent feature.

3. The device of claim 1, the device surface further comprising a plurality of the features, wherein at least one of the features has a major dimension that is different from the major dimension of an adjacent feature.

4. The device of claim 1, the device surface further comprising a plurality of the features, wherein at least one of the features has a depth that is different from the depth of an adjacent feature.

5. The device of claim 1, wherein the at least one feature is oriented about its central axis at an angle that is different from the angle of an adjacent feature.

6. The device of claim 1, wherein the at least one feature has a major dimension that is different from the major dimension of an adjacent feature.

7. The device of claim 1, wherein the at least one feature has a depth that is different from the depth of an adjacent feature.

8. A medical device comprising:
a device surface having a plurality of echogenic features, wherein at least one of the features is a depression in the device surface and has a rim and a bottom surface,
wherein the bottom surface is within the rim and faces outward of the depression, and
further comprising a lobe extending over the depression, wherein a portion of the lobe faces the bottom surface and defines a pocket between the bottom surface and the lobe.

9. The device of claim 8, wherein the lobe extends over substantially half of the depression.

10. The device of claim 8, wherein the at least one feature has three feature surfaces, wherein each feature surface intersects the other feature surfaces, and wherein each feature surface is concave toward the center of the feature.

11. The device of claim 8, wherein the at least one feature has three feature surfaces, wherein each feature surface intersects the other feature surfaces, and wherein at least one feature surface has a dimension aligned with the device surface that is different from a dimension aligned with the device surface of another feature surface.

12. The device of claim 8, wherein the lobe is formed by a pushing a raised portion around the rim into the depression.

13. A medical device comprising:
a cannula having a body portion and a tip portion, wherein the diameter of the cannula is tapered along a length of the cannula in the tip portion relative to the general diameter of the body portion; and
at least one depression formed into the surface in the tapered length of the tip portion, wherein the depression has a depression surface, and wherein the surface normal at all points along the depression surface has vector components that point in a direction that is perpendicular to the cannula axis and/or toward the furthest extent of the tip portion.

14. The device of claim 13, wherein the depression has a rim defined by the intersection between the depression surface and a surface of the cannula, wherein the rim is generally shaped as a teardrop, wherein the depression has a depression axis extending symmetrically relative to the depression and intersecting the rim, wherein the depression axis follows a path within a plane extending through the axis of the cannula.

15. The device of claim 13, further comprising a plurality of depressions arranged about the tip portion.

16. The device of claim 15, the surface further comprising a plurality of depressions, wherein at least one of the depressions has a major dimension that is different from the major dimension of an adjacent depression.

17. The device of claim 15, the surface further comprising a plurality of depressions, wherein at least one of the depressions has depth that is different from the depth of an adjacent depression.

18. The device of claim 13, wherein the depression surface is bounded on all sides by a rim defined by the intersection between the depression surface and a surface of the cannula.

19. The device of claim 18, wherein the depression surface has a first portion having a normal vector that points in a direction toward the tip portion and a second portion having a normal vector that points in a direction that is perpendicular to the cannula axis.

* * * * *